United States Patent [19]

Amelse et al.

[11] Patent Number: 4,899,010
[45] Date of Patent: Feb. 6, 1990

[54] PROCESS FOR ISOMERIZATION OF UNEXTRACTED, ETHYLBENZENE-CONTAINING XYLENE FEEDS

[75] Inventors: Jeffrey A. Amelse, Batavia; Mark G. Reichmann, Oak Park, both of Ill.

[73] Assignee: Amoco Corporation, Chicago, Ill.

[21] Appl. No.: 250,933

[22] Filed: Sep. 29, 1988

[51] Int. Cl.$^4$ .............................. C07C 5/22
[52] U.S. Cl. ............................ 585/480; 585/481
[58] Field of Search .......................... 585/480, 481

[56] References Cited

U.S. PATENT DOCUMENTS

| | | | |
|---|---|---|---|
| 4,268,420 | 5/1981 | Klotz | 585/481 |
| 4,285,919 | 8/1981 | Klotz et al. | 502/202 |
| 4,593,138 | 6/1986 | Czsci et al. | 585/481 |
| 4,620,921 | 11/1986 | Chang et al. | 585/481 |
| 4,654,456 | 3/1987 | Nimry | 585/481 |
| 4,717,780 | 1/1988 | Olson et al. | 585/481 |

Primary Examiner—Curtis R. Davis
Attorney, Agent, or Firm—Reed F. Riley; William H. Magidson; Ralph C. Medhurst

[57] ABSTRACT

An improved process employing a supported, platinum-containing, crystalline, silicate molecular sieve catalyst composition effective in removing ethylbenzene from unextracted xylene feeds during isomerization, primarily by hydrodeethylation, and also the primarily C$_9$ paraffins and naphthenes. Choosing (1) a set of process conditions within narrow ranges of temperature T, total pressure P, and hydrogen to hydrocarbon mol ratio H/HC such that Z, which is defined as a function of T, P and H/HC, is less than about 0.01, and (2) a platinum-containing catalyst composition, greatly reduces the feed C$_9$ paraffins and naphthenes content during isomerization, removes most of the ethylbenzene by hydrodeethylation to ethane and benzene, and minimizes xylene loss to hydrogenation and cracking, all without substantially changing the excellent isomerization properties of the sieve catalyst composition.

11 Claims, 1 Drawing Sheet

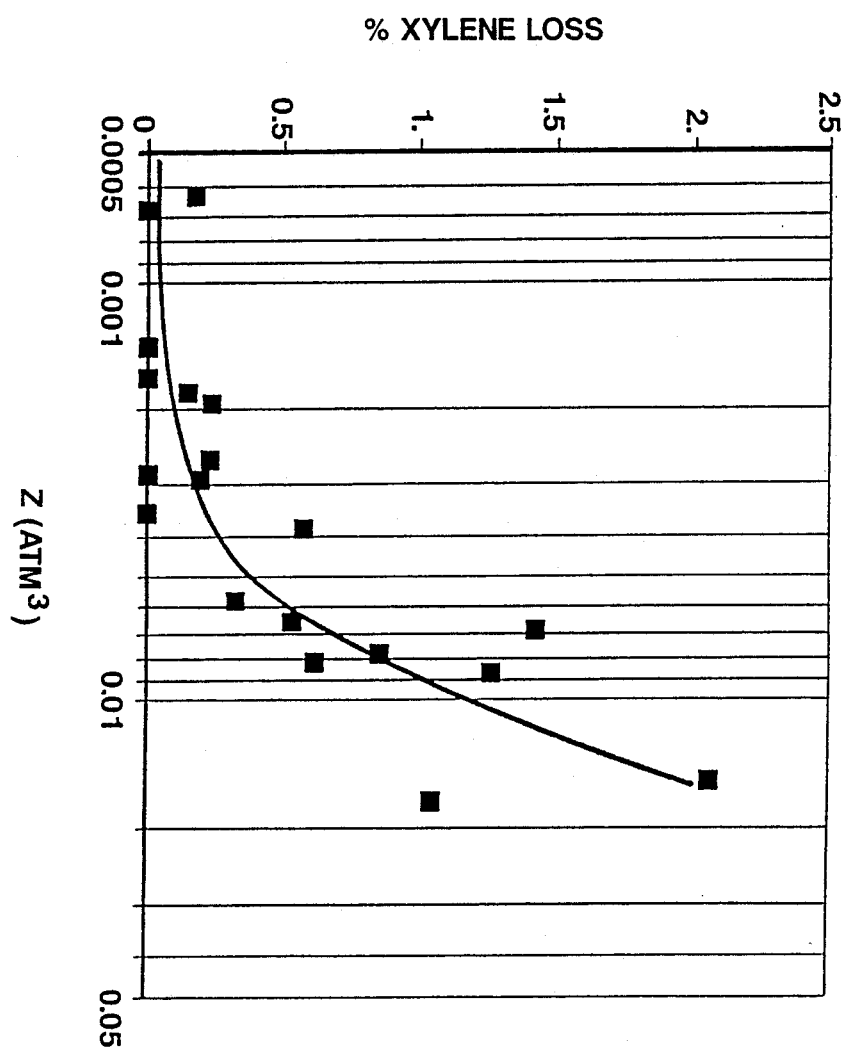

PROCESS FOR ISOMERIZATION OF UNEXTRACTED, ETHYLBENZENE-CONTAINING XYLENE FEEDS

BACKGROUND OF THE INVENTION

This invention relates to an improved molecular-sieve-catalyzed process for isomerizing an unextracted, ethylbenzene-containing xylene feed to a mixture rich in paraxylene which converts the ethylbenzene content primarily to benzene and ethane and provides high conversion of non-aromatic hydrocarbons in the feed to easily separable products. More particularly, this invention relates to a process for isomerizing an unextracted xylene feed containing a substantial quantity of ethylbenzene to a mixture rich in paraxylene over a supported, platinum-containing, medium pore size, crystalline, silicate molecular sieve catalyst composition under narrowly defined process conditions of temperature, total pressure, and hydrogen to hydrocarbon mol ratio in which the ethylbenzene present in the feed is largely converted to benzene and ethane by hydrodeethylation, and the primarily $C_9$ paraffins and naphthenes (P/Ns) present are effectively removed by conversion to light hydrocarbons.

Typically, paraxylene is derived from mixtures of $C_8$ aromatics separated from such raw materials as petroleum naphthas, particularly reformates, usually by isomerization followed by, for example, lower-temperature crystallization of the paraxylene with recycle of the crystallizer liquid phase to the isomerizer. Principal raw materials are catalytically reformed naphthas and petroleum distillates. The fractions from these sources that contain the $C_8$ aromatics vary quite widely in composition but will usually contain 10 to 35 weight percent ethylbenzene and up to about 10 weight percent primarily $C_9$ paraffins and naphthenes with the remainder being primarily xylenes divided approximately 50 weight percent meta, and 25 percent each of the ortho and para isomers. The primarily $C_9$ paraffins and naphthenes can be removed substantially by extraction to produce what are termed "extracted" xylene feeds. The extraction step adds to processing costs. Feeds that do not have the primarily $C_9$ paraffins and naphthenes removed by extraction are termed "unextracted" xylene feeds.

The ethylbenzene in a xylene mixture is very difficult to separate from the other components due to similar volatility, and, if it can be converted during isomerization to products more readily separated from the xylenes, buildup of ethylbenzene in the recycle loop is prevented and process economics are greatly improved. The primarily $C_9$ paraffins and naphthenes present in unextracted feeds unless removed also build up in the recycle loop and are usually extracted prior to isomerization as most commercial isomerization processes do not provide a catalyst which effectively converts them to easily separable-by-distillation products. Thus, it would be valuable to have a catalyst/process for xylene isomerization which would effectively convert both the ethylbenzene and primarily $C_9$ paraffins and naphthenes to easily separable products without affecting the isomerization efficiency.

Xylene isomerization catalysts can be classified into three types based upon the manner in which they convert ethylbenzene: (1) naphthene pool catalysts, (2) transalkylation catalysts, and (3) hydrodeethylation catalysts.

Naphthene pool catalysts are capable of converting a portion of the ethylbenzene to xylenes via naphthene intermediates. These catalysts contain a strong hydrogenation function, such as platinum, and an acid function, such as chlorided alumina, amorphous silica-alumina, or a molecular sieve. The role of the hydrogenation function in these catalysts is to hydrogenate the $C_8$ aromatics to establish essentially equilibrium between the $C_8$ aromatics and the $C_8$ cyclohexanes. The acid function interconverts ethylcyclohexane and the dimethylcyclohexanes via cyclopentane intermediates. These $C_8$ cycloparaffins form the so-called naphthene pool.

It is necessary to operate naphthene pool catalysts at conditions that allow the formation of a sizable naphthene pool to allow efficient conversion of ethylbenzene to xylenes. Unfortunately, naphthenes can crack on the acid function of the catalyst, and the rate of cracking increases with the size of the naphthene pool. Naphthene cracking leads to high xylene loss, and the byproducts produced by naphthene cracking are low-valued paraffins. Thus, naphthene pool catalysts are generally less economic than the transalkylation-type and hydrodeethylation-type catalysts.

The transalkylation catalysts generally contain a shape selective molecular sieve. A shape selective catalyst is one that prevents some reactions from occurring based on the size of the reactants, products, or intermediates involved. In the case of common transalkylation catalysts, the molecular sieve contains pores that are apparently large enough to allow ethyl transfer to occur via a dealkylation/realkylation mechanism, but small enough to substantially suppress methyl transfer which requires the formation of a bulky biphenylalkane intermediate. The ability of transalkylation catalysts to catalyze ethyl transfer while suppressing methyl transfer allows these catalysts to convert ethylbenzene while minimizing xylene loss via xylene disproportionation.

When ethyl transfer occurs primarily by dealkylation/realkylation, it is possible to intercept and hydrogenate the ethylene intermediate involved with this mechanism of ethyl transfer by adding a hydrogenation function to the catalyst. The primary route for converting ethylbenzene then becomes hydrodeethylation, which is the conversion of ethylbenzene to benzene and ethane. It is desirable to selectively hydrogenate the ethylene intermediate without hydrogenating aromatics (without establishing a naphthene pool) to prevent the cracking of the naphthenes that occurs over the acid function of the catalyst. Commercial hydrodeethylation catalysts selectively hydrogenate ethylene without substantial hydrogenation of aromatics at reported commercial conditions. At these same conditions, a small amount of impregnated platinum compound will allow substantial hydrogenation of aromatics.

In order to form a hydrodeethylation catalyst, it is essential to use an acidic component that behaves as a shape selective catalyst, i.e., one that suppresses the formation of the bulky biphenylalkane intermediate required for transmethylation, because transethylation can occur via a similar intermediate. For catalysts with pores large enough to allow the formation of these biphenylalkane intermediates, transethylation appears to occur primarily via these intermediates. In this case, ethylene is not an intermediate for transethylation, and the addition of a hydrogenation component cannot produce a hydrodeethylation catalyst.

Now it has been found that by choosing isomerization temperature, total pressure, and mol ratio, hydrogen/hydrocarbon, in narrowly defined ranges, a platinum-containing, acidic, medium pore size, molecular sieve catalyst composition can be used in a process in which most of the ethylbenzene is removed by hydrodeethylation, and the size of the naphthene pool is reduced resulting in less xylene loss. In addition, it has been found that this catalyst and certain sets of temperature, total pressure, and hydrogen to hydrocarbon mol ratio variables within this narrowly defined set of process condition ranges provide very high conversion of paraffins and naphthenes to light products which can be readily separated from the reactor effluent. Thus, ethylbenzene is removed by a particularly attractive process, a greater amount of paraffins and naphthenes can be tolerated in the isomerizer feed, and the xylene isomerization effectiveness is essentially unchanged.

BRIEF DESCRIPTION OF THE DRAWING

The FIGURE shows a plot of the percent xylene loss via hydrogenation and cracking adjusted to 25 weight percent ethylbenzene conversion versus Z for 20 sets of P,T and hydrogen to hydrocarbon mol ratio H/HC, conditions that cover a temperature range of 699° F. to 801° F., a total pressure range of 40 psig to 125 psig, and a range of H/HC from 0.93 to 2.08. Z was calculated using the formulas set forth below. The percent xylene loss due to hydrogenation and cracking was calculated as the net yield in weight percent of total paraffins and naphthenes, P/Ns, (weight percent P/Ns in reactor effluent minus weight percent P/Ns in the feed) minus the net yield of ethane in weight percent (ethane is assumed to come entirely from the hydrodeethylation of ethylbenzene) divided by the weight percent of xylene isomers in the feed times 100 percent. To adjust for differences in ethylbenzene conversion, the percent xylene loss to P/Ns adjusted to 25 weight percent ethylbenzene conversion (adjusted percent xylene loss to hydrogenation and cracking) is calculated by multiplying the percent xylene loss to P/Ns by 25 weight percent ethylbenzene conversion and dividing by the actual percent ethylbenzene conversion.

BRIEF DESCRIPTION OF THE INVENTION

In a vapor-phase process to isomerize, in the presence of hydrogen, a stream containing one or more xylenes, a substantial amount of ethylbenzene, and primarily $C_9$ paraffins and naphthenes to a mixture rich in paraxylene, the improvement comprising reacting said feed over a catalyst composition which is a supported, crystalline, silicate molecular sieve having pores defined by rings containing ten oxygen atoms and containing a heteroatom selected from the group consisting of boron, aluminum, iron and gallium, said heteroatom present in a ratio of about one heteroatom for each twelve to five hundred silicon atoms, which catalyst composition contains about 0.02 to about 5 weight percent platinum, calculated as the metal, at a temperature T between about 700 and about 1000° F., a total pressure P between ambient and about 100 psig, and a hydrogen/hydrocarbon mol ratio H/HC between about 0.25 and about 5 such that T, P and H/HC are chosen so that Z, a function of T, P, and H/HC, is less than about 0.01.

DETAILED DESCRIPTION OF THE INVENTION

Unextracted xylene-containing feeds to this process include one or more of the xylene isomers and between about five and about thirty-five weight percent of ethylbenzene depending upon the source of the feed. These feeds also include between about one and about ten percent primarily $C_9$ paraffins and naphthenes. Such paraffins and naphthenes include materials such as n-nonane, methyl octanes, dimethylheptanes, trimethylcyclohexane, ethylmethylcyclohexane and the like.

The molecular sieves useful in this invention are silicates that contain boron, aluminum, iron, or gallium heteroatoms in a ratio to silicon atoms of about 1 heteroatom to every 12–500 silicon atoms. More particularly, these molecular sieves contain about one heteroatom to every 12–200 silicon atoms. These molecular sieves include but are not limited to silicates, borosilicates, aluminosilicates, gallosilicates, and ferrosilicates having framework topology designations of MFI, MEL, or MTT, as proposed in W. H. Meier, and D. H. Olson, "Atlas of Zeolite STructure Types," Structure Commission of the International Zeolite Association (1978) and A. C. Rohrman, Jr., R. B. LaPierre, J. L. Schlenker, J. D. Wood, E. W. Valyocsik, M. K. Rubin, J. B. Higgins, and W. J. Rohrbaugh, Zeolites, 5, 353 (1985), and/or having framework topologies similar to ZSM-5 (U.S. Pat. No. 3,702,886), ZSM-11 (U.S. Pat. No. 3,709,971), ZSM-22, ZSM-23, ZSM-48, theta-1, ferrierite, Nu-10, KZ-2, ISI-1, EU-2, ZBM-30, EU-11, ISI-4, KZ-1 and AMS-1B (U.S. Pat. Nos. 4,268,420; 4,269,813; 4,285,919 and published European Application 68796). The latter three patents and applications are incorporated herein by reference.

The preferred molecular sieve for use herein is the hydrogen form of the AMS-1B crystalline, borosilicate molecular sieve, HAMS-1B.

Molecular sieve pores defined by fewer than ten oxygen rings are believed to be too small to allow ethylbenzene dealkylation, while pores defined by rings containing more than ten oxygen atoms are believed to be large enough to allow substantial transethylation and transmethylation via biphenylalkane intermediates.

The catalyst compositions used in the disclosed process contain platinum with a loading of about 0.02 weight percent to about 5 weight percent, with a loading of about 0.1 weight percent to about 1 weight percent preferred. The platinum may be added to the molecular sieve/support combination by standard impregnation or by ion exchange techniques. Alternatively, it may be added to the synthesis gel used to prepare the molecular sieve. It is believed that the platinum loading can be reduced by improving the dispersion of platinum on the catalyst composition surface as can be understood by one skilled in the art. Platinum compounds useful for impregnation include soluble platinum compounds such as chloroplatinic acid, platinum chloride, tetrammineplatinum (II) salts, and the like. The support is generally present in an amount between about 10 and 95 weight percent, more preferably about 40 and 95 weight percent based upon the total weight of catalyst.

Supports useful for the platinum-containing catalyst compositions generally include materials such as silica, alumina or silica-alumina and the like. The preferred support for the HAMS-1B crystalline, borosilicate molecular sieve is alumina. The support is generally present in an amount between about 10 and 95 weight percent, more preferably between about 40 and 95 weight percent of the total catalyst composition.

The temperature range useful in carrying out the invention taught herein is in the range from about 700 to about 1000° F., more preferably, between about 750 and 900° F.. The total pressure useful in the invention should be held between about 1 and about 100 psig, more preferably, between about 25 and about 75 psig. Hydrogen must be used in the inventive isomerization process and the mol ratio, hydrogen to total hydrocarbon, should be held between about 0.25 and about 5, more preferably, between about 0.5 and about 3. Space velocities useful in this invention are those typically used for the type of reaction used in xylene isomerization as can be understood by one skilled in the art.

It is important in carrying out the invention to recognize that the process temperature, total pressure and hydrogen to hydrocarbon mol ratio are not independent and that, within the ranges given above, choosing a value for one fixes the useful ranges of the other two process variables. To calculate which sets of T, P, and hydrogen to hydrocarbon ratio H/HC are useful in the invention, a quantity Z is calculated as follows:

$$Z = K P_H^3 \quad (1)$$

where K as a function of temperature is given by the expression:

$$\mathrm{Ln}\, K = 43.288 + \frac{21540}{T} - 14.303\, \mathrm{Ln}\, T + 0.01466 T - 2.521 \times 10^{-6} T^2 + 2.165 \times 10^{-10} T^3 \quad (2)$$

and the partial pressure of hydrogen, $P_H$, is given by:

$$P_H = \frac{H/HC}{1 + H/HC} \cdot P \quad \text{where } H/HC \text{ is as previously defined} \quad (3)$$

and P is the total pressure.

Using the equations above, it has been determined that only sets of P, T, and H/HC where Z is less than about 0.01, more preferably less than about 0.0075, and most preferably less than about 0.005, give the desired results in the inventive process which converts the primarily $C_9$ paraffins and naphthenes to light products, the ethylbenzene to benzene and ethane primarily via the hydrodeethylation mechanism, and minimizes the xylene loss via hydrogenation and cracking.

Preferably over about 70 weight percent, more preferably over about 80 weight percent of the total ethylbenzene reacted, is converted by the instant process via hydrodeethylation to ethane and benzene. In respect of the paraffins and naphthenes, over about 60 weight percent, more preferably over about 80 weight percent, is converted by the instant process to light, easily separable by distillation, hydrocarbons.

For carrying out the processes of this invention, it is preferred to choose catalyst and process conditions such that the adjusted % xylene loss to paraffins and naphthenes is less than about 1 weight percent, more preferably less than about 0.75 weight percent, and most preferably less than about 0.5 weight percent.

The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES

Example 1

A catalyst comprising about 10 wt% AMS-1B crystalline borosilicate molecular sieve and 0.5 wt% platinum, calculated as the metal, on an alumina support was prepared as follows. A 22.0 g portion of distilled water was added to 10 g of the hydrogen form of AMS-1B. A 1097.8 g portion of alumina sol (8.2 wt% solids) was added and this mixture was blended in a homogenizer for approximately 3 minutes. A 90 ml amount of concentrated ammonium hydroxide was added to gel this mixture, and the gel was blended in a mixmaster for about 3 minutes. The gelled AMS-1B on alumina catalyst was dried at 329° F. for 4 hr, ramped linearly to 950° F. over 4 hr, than calcined at 950° F. for 4 hr.

An impregnation solution was prepared by adding 0.90 g of chloroplatinic acid to 66.41 g of distilled water. A 20.14 g portion of this solution was added to 20.04 g of the above AMS-1B on alumina catalyst, which had been ground to 18-40 mesh. The impregnated catalyst was dried at 329° F. overnight.

Example 2

Xylene isomerization was carried out over the catalyst composition of Example 1 with a xylene feed that contained about 79 percent xylenes, about 14 percent ethylbenzene, and about 4 percent of primarily $C_9$ paraffins and naphthenes. The data in the Table below shows that a large fraction of the ethylbenzene is converted by hydrodeethylation and an extremely high percentage of $C_9$ P and Ns are converted. The Example further shows that values of Z outside the claimed range lead to excessive xylene loss via hydrogenation and cracking.

TABLE

| Component | Composition in wt % | | | |
| --- | --- | --- | --- | --- |
|  | Feed | Effl. | Feed | Effl. |
| Light P/N's | 0.008 | 7.229 | 0.008 | 5.115 |
| $C_9$ P/N's | 4.024 | 0.637 | 4.025 | 0.415 |
| Total P/N's | 4.032 | 7.866 | 4.033 | 5.530 |
| Benzene | 0.268 | 2.948 | 0.282 | 3.025 |
| Toluene | 0.563 | 1.177 | 0.568 | 1.038 |
| Ethylbenzene | 14.446 | 9.097 | 14.461 | 10.405 |
| Para-xylene | 8.554 | 18.579 | 8.551 | 18.853 |
| Meta-xylene | 47.877 | 40.948 | 47.870 | 41.346 |
| Ortho-xylene | 22.873 | 17.465 | 22.851 | 18.182 |
| Other | 1.387 | 1.920 | 1.384 | 1.621 |
| T (°F.) | 700.00 | | 750.00 | |
| P (PSIG) | 50.00 | | 50.00 | |
| H/HC | 1.93 | | 1.91 | |
| WHSV | 2.46 | | 5.93 | |
| % EB Conversion | 37.03 | | 28.05 | |
| % Xylene Loss | 4.22 | | 1.00 | |
| % EB Conv./% xylene loss | 8.77 | | 28.06 | |
| % $C_9$ P/N Conversion | 84.16 | | 89.68 | |
| % of EB Converted to Benzene + Ethane | 88.41 | | 89.56 | |
| % of xylene loss to P/N's | 72.18 | | 21.75 | |
| % xylene loss to P/N's adjusted to 25% EB conv. | 2.06 | | 0.19 | |
| Z | 0.0157 | | 0.00295 | |
| Light P/N's | 0.000 | 4.187 | 0.008 | 4.987 |
| $C_9$ P/N's | 4.003 | 1.625 | 4.025 | 0.562 |
| Total P/N's | 4.003 | 5.812 | 4.033 | 5.549 |
| Benzene | 0.249 | 2.618 | 0.282 | 2.923 |
| Toluene | 0.549 | 0.928 | 0.568 | 1.092 |
| Ethylbenzene | 14.436 | 10.609 | 14.461 | 10.811 |
| Para-xylene | 8.548 | 18.805 | 8.551 | 18.661 |
| Meta-xylene | 47.909 | 41.273 | 47.870 | 40.804 |

TABLE-continued

| Component | Composition in wt % | | | |
|---|---|---|---|---|
| | Feed | Effl. | Feed | Effl. |
| Ortho-xylene | 22.925 | 18.238 | 22.851 | 18.711 |
| Other | 1.381 | 1.717 | 1.384 | 1.449 |
| T (°F.) | | 750.00 | | 801.00 |
| P (PSIG) | | 100.00 | | 50.00 |
| H/HC | | 2.02 | | 1.93 |
| WHSV | | 9.00 | | 14.93 |
| % EB Conversion | | 26.51 | | 25.24 |
| % Xylene Loss | | 1.86 | | 0.86 |
| % EB Conv./% xylene loss | | 14.22 | | 29.39 |
| % $C_9$ P/N Conversion | | 59.40 | | 86.04 |
| % of EB Converted to Benzene + Ethane | | 87.55 | | 91.83 |
| % of xylene loss to P/N's | | 59.80 | | 18.89 |
| % xylene loss to P/N's adjusted to 25% EB conv. | | 1.05 | | 0.16 |
| Z | | 0.0174 | | 0.000626 |

What is claimed is:

1. In a vapor-phase process to isomerize, in the presence of hydrogen, a stream containing a major amount of one or more xylenes and a minor amount of ethylbenzene and primarily $C_9$ paraffins and naphthenes to a mixture rich in paraxylene, the improvement comprising isomerizing said feed over a catalyst composition that is a supported, crystalline, silicate molecular sieve having pores defined by rings containing ten oxygen atoms and containing a heteroatom selected from the group consisting of boron, aluminum, iron and gallium, said heteroatom present in a ratio of about one heteroatom for each twelve to five hundred silicon atoms, which catalyst composition is impregnated with about 0.02 to about 5 weight percent platinum, calculated as the metal, at a temperature T between about 700 and about 1000° F., a total pressure P between ambient and about 100 psig, and a hydrogen/hydrocarbon mol ratio H/HC between about 0.25 and about 5, such that T, P, and H/HC are chosen so that Z, a function of T, P and H/HC, is less than about 0.01.

2. The process of claim 1 wherein said heteroatom is boron.

3. The process of claim 1 wherein said heteroatom is aluminum.

4. The process of claim 1 wherein said heteroatom is gallium.

5. The process of claim 1 wherein said heteroatom is present in a ratio of about one heteroatom for each twelve to two hundred silicon atoms, said weight percent platinum is between about 0.1 and about 1, said temperature is between about 750 and about 900° F., said total pressure is between about 25 and about 75 psig, and said hydrogen/hydrocarbon mol ratio is between about 0.5 and about 3.

6. The process of claim 5 wherein said heteroatom is boron.

7. The process of claim 5 wherein said heteroatom is aluminum.

8. The process of claim 5 wherein said heteroatom is gallium.

9. The process of claim 1 wherein said supported sieve is an HAMS-1B crystalline, borosilicate molecular sieve supported on alumina.

10. The process of claim 1 wherein said sieve is a medium pore, crystalline, aluminosilicate molecular sieve having a ratio of silicon to alumina atoms between about twelve to about five hundred supported on silica, alumina, or silica-alumina.

11. The process of claim 10 wherein said sieve is supported on alumina.

* * * * *